(12) United States Patent
Beukeveld

(10) Patent No.: US 8,372,627 B2
(45) Date of Patent: Feb. 12, 2013

(54) METHODS FOR IN SITU ACCELERATION OF BIOLOGICAL DEGRADATION OF CHLOROHYDROCARBON IN A SOIL

(76) Inventor: Gerhardus Johannes Jozef Beukeveld, Hoorn (NL)

( * ) Notice: Subject to any disclaimer, the term of this patent is extended or adjusted under 35 U.S.C. 154(b) by 1117 days.

(21) Appl. No.: 11/908,490

(22) PCT Filed: Mar. 10, 2006

(86) PCT No.: PCT/NL2006/000124
§ 371 (c)(1),
(2), (4) Date: Feb. 6, 2008

(87) PCT Pub. No.: WO2006/098615
PCT Pub. Date: Sep. 21, 2006

(65) Prior Publication Data
US 2008/0194007 A1      Aug. 14, 2008

(30) Foreign Application Priority Data

Mar. 13, 2005   (NL) ..................................... 1028531

(51) Int. Cl.
*A62D 3/00* (2007.01)
(52) U.S. Cl. ..................................... 435/262.5; 435/264
(58) Field of Classification Search .................. None
See application file for complete search history.

(56) References Cited

U.S. PATENT DOCUMENTS

| | | | |
|---|---|---|---|
| 5,342,524 A | 8/1994 | Gaddy | |
| 5,602,296 A * | 2/1997 | Hughes et al. | 588/316 |
| 5,902,744 A | 5/1999 | Gray et al. | |
| 5,998,199 A | 12/1999 | Moser et al. | |
| 6,033,899 A | 3/2000 | Moser et al. | |
| 6,060,292 A | 5/2000 | Gray et al. | |
| 6,083,738 A | 7/2000 | Moser et al. | |
| 6,719,902 B1 | 4/2004 | Alvarez et al. | |
| 6,783,678 B2 * | 8/2004 | Sorenson | 210/610 |
| 2003/0232423 A1 | 12/2003 | Priester, III et al. | |
| 2005/0064576 A1 * | 3/2005 | Fennell et al. | 435/262.5 |
| 2006/0094106 A1 | 5/2006 | Priester, III et al. | |

OTHER PUBLICATIONS

Smidt et al., Annual Review of Microbiology, 2004, vol. 58 p. 43-73.*
Maymo-Gatell, X., Report 1993, Abstract.*
Maymo-Gatell et al., Nature, 1997, vol. 276, p. 1568-1571.*
Holliger et al., Arch Microbiol, 1998, vol. 169, p. 313-321.*
PCT International Search Report, PCT/nl2006/000124, dated Jun. 12, 2006.
Fennell et al.; Dehalococcoides ethenogenes Strain 195 Reductively Dechlorinates Diverse Chlorinated Aromatic Pollutants; Environ. Sci. Technol. 2004; 38; 2075-2081.
Maymo-Gatell et al., Characterization of an H2-Utilizing Enrichment Culture that Reductively Dechlorinates Tetrachloroethene to Vinyl Chloride and Ethenein the Absence of Methanogenesis and Acetogenesis; Applied and Environmental Microbiology, Nov. 1995, p. 3928-3933.
Maymo-Gatell et al., Reductive Dechlorination of Chlorinated Ethenes and 1, 2-Dichloroethane by "*Dehalococcoides ethenogenes*" 195; Applied and Environmental Microbiology, Jul. 1999, p. 3108-3113.
Maymo-Gatell et al., Reductive Dechlorination of*cis*-1, 2-Dichloroethene and Vinyl Chloride by"*Dehalococcodes ethenogenes*"; Environ. Sci. Technol. 2001; 35; 516-521.

* cited by examiner

*Primary Examiner* — Kade Ariani
(74) *Attorney, Agent, or Firm* — TraskBritt

(57) ABSTRACT

The invention provides methods for in situ acceleration of biological degradation of chlorinated hydrocarbons in a soil. The invention particularly provides a method for in situ acceleration of biological degradation of chlorinated hydrocarbons in a soil comprising adding $H_2$, $CO_2$ and acetate.

18 Claims, No Drawings

METHODS FOR IN SITU ACCELERATION OF BIOLOGICAL DEGRADATION OF CHLOROHYDROCARBON IN A SOIL

The invention relates to the field of environment, soil science and soil sanitation technology. The invention particularly relates to in situ acceleration of biological degradation of chlorinated hydrocarbons in a soil.

Chlorinated hydrocarbons are good fat solvents. Therefore these substances are frequently used in the metal industry and in dry cleaning. Thereby, up to the 1980s, large amounts of chlorinated hydrocarbons have ended up in the ground to severely pollute the soils there. Removing these pollutants is difficult and complex. This is because chlorinated hydrocarbons are heavier than water, so that they may be present in the soil to a great depth in high concentrations. In addition, they only slowly pass into dissolution and they thus form secondary pollution sources for long periods, which are to be sanitized to prevent further pollution.

Currently, biological degradation of these chlorinated hydrocarbons is the most effective manner of sanitation. In the field, here, use is made of addition of a single substance to a soil for in situ acceleration of the biological degradation process. A drawback that is attached to the current known methods is that non-predictable lag phases occur, in which no conversion of chlorinated hydrocarbon is measurable. A further drawback is that the half-life of chlorinated hydrocarbon is indeed reduced by most known methods, but it still long. Therefore, a first object of the invention is to shorten the lag phase of the biological degradation of chlorinated hydrocarbon. A second object is to shorten the half-life of biological degradation of chlorinated hydrocarbon. The objects of the invention are achieved by addition of at least $H_2$ (hydrogen), $CO_2$ (carbon dioxide) and acetate to a soil, so that biological degradation of chlorinated hydrocarbon in a soil is strongly stimulated. Then, the stimulation is such that the lag phase of a method for stimulation of biological degradation of chlorinated hydrocarbon becomes better predictable and is shortened compared to the lag phases occurring with the methods known in the field. Further, by a method according to the invention, the half-life of chlorinated hydrocarbon is shortened compared to methods which were so far known in the field. Without wishing to be bound to any theory, it appears that the good effect of the method according to the invention compared to the methods used in the field can be explained as follows. It appears that in the biostimulations currently used so far, carbon dioxide, acetate and/or hydrogen are the limiting factors. This results in long, non-predictable lag phases. With the present approach of the invention, a solution is found for this by artificially offering $CO_2$ and $H_2$, for instance as gases, and, dissolved or not dissolved, acetate in overmeasure. As a result, with a method according to the invention, generally the amount of chlorinated hydrocarbon is the rate-determining step. With a method according to the invention, a large amount of polluting chlorinated hydrocarbon in a soil will thus result in a high rate of conversion of chlorinated hydrocarbon. Of course, such a fast conversion of the polluting chlorinated hydrocarbon is very desirable since, from a soil contaminated with chlorinated hydrocarbon, its pollutants are to be removed as soon as possible so that the soil is soon ready again for various uses.

So, the invention provides an in situ soil decontamination method for the biological degradation of chlorinated hydrocarbons in soils, characterized in that, for this biological decontamination, hydrogen and carbon dioxide and acetate are applied to the soils from external sources for stimulation and support of the respiration chain and growth of anaerobic bacteria so that they biologically degrade the chlorinated hydrocarbons in an accelerated manner. The invention thus provides a method for in situ biological degradation or in situ acceleration of biological degradation of chlorinated hydrocarbons in a soil, comprising adding at least the following substances: $H_2$, $CO_2$ and acetate to this soil, while this soil comprises anaerobic bacteria, and while these substances are simultaneously present in the soil. Acceleration of biological degradation as used in the invention comprises both the acceleration of biological degradation compared to a situation in which no biological degradation took place and acceleration of biological degradation compared to a situation in which biological degradation took place, but to a smaller extent than desired and/or not to an optimal extent. A chlorinated hydrocarbon as used in the invention comprises any chlorinated hydrocarbon, a substance comprising at least one chlorine atom, at least one carbon atom and at least one hydrogen atom. A chlorinated hydrocarbon according to the invention may be both of natural origin and of synthetic origin. Examples of chlorinated hydrocarbons are polychlorinated biphenyl compounds (PCBs), chlorofluorocarbons (CFCs), chlorinated paraffins, tetrachloroethene, trichloroethene and dichloroethenes. A soil as used in the invention comprises any environment which is located or can be located below the surface of the earth. Preferably, a soil as used in the invention comprises a type of soil, such as sand and peat. A soil may, for instance, also comprise an isolated or non-isolated volume of ground which is located above the surface of the earth, such as a lump of ground which has been dug up in a polluted area for sanitation. In situ, as used in the invention, means that the soil need not be moved and can be treated on location, i.e. the biological degradation of chlorinated hydrocarbon can be stimulated on location. In situ may be any desired location, for instance the location where a contaminated soil has been found or the location where a dug-up contaminated soil is stored. According to a method of the invention it is not necessary, but it is possible, to change a soil structure and/or to fragment a soil and/or to sieve it before accelerating a biological degradation.

The addition of at least $H_2$, $CO_2$ and acetate to the soil mentioned in a method according to the invention is an essential feature of the invention. This is because, while it is true that $H_2$, $CO_2$ and acetate may already be present in the soil, the amounts in which these three substances are present in normal conditions do not reach the amounts needed for the stimulation of biological degradation of chlorinated hydrocarbon in a soil as realized by the invention. Acetate comprises any compound comprising the structure $CH_3COO-$. An acetate is, for instance, the salt of acetic acid, for instance sodium acetate ($CH_3COONa$). Other examples of an acetate are an acetate ester or ammonium acetate. Use of an ammonium acetate has the advantage that, in addition to acetate, this compound also provides the soil with nitrogen. If there is not sufficient nitrogen present in a soil, then the acetate is thus added as ammonium acetate in a preferred embodiment of the invention. $H_2$, $CO_2$ and acetate may be added in pure form and/or as part of more complex compounds and/or in a mixture with other substances. In a preferred embodiment of the invention, $H_2$ and/or $CO_2$ and/or acetate are added in pure form, optionally at the same time as other substances. That is to say that $H_2$ is preferably added as $H_2$, $CO_2$ is preferably added as $CO_2$ and acetate preferably as $CH_3COO-$. $H_2$, $CO_2$ and acetate may be added to the soil mentioned simultaneously or successively, as long as these added substances are simultaneously present in the soil at least at one time. The substances according to the invention can be added in any phase conceivable by a skilled person, such as gaseous and/or liquid. Thus, for instance, $CO_2$ is added in a gaseous and/or liquid form.

Anaerobic bacteria need no or hardly no oxygen to be able to live. An anaerobic bacterium according to the invention comprises all anaerobic bacteria, so a bacterium is, for instance, obligatory anaerobic, facultatively anaerobic or microaerobic. An obligatory anaerobic bacterium is not capable of surviving in an oxygen-rich environment. A facultatively anaerobic bacterium can survive both with and without oxygen. Microaerobic bacteria do need oxygen, but a very small amount is sufficient for them. Most soils according to the invention will already comprise a number of anaerobic bacteria without intervention by means of a method according to the invention. Optionally, to the soil mentioned, anaerobic bacteria are added.

In one embodiment, the invention thus provides a method according to the invention in which these anaerobic bacteria have been added at least partly to this soil. The addition may be done to a soil which comprises no or fewer anaerobic bacteria without intervention and/or to a soil which comprises a different composition of bacteria before intervention. The bacteria to be added may be bacteria which naturally occur in the respective soil, but may alternatively be added to the soil from another location. This other location may be another soil, but also any other source which can provide anaerobic bacteria.

The anaerobic bacteria according to the invention are preferably lithotrophic bacteria. Therefore, in one embodiment, the invention provides a method according to the invention in which these anaerobic bacteria comprise lithotrophic bacteria. Lithotrophic bacteria are chemolithotrophs or photolithotrophs. For the invention, particularly the chemolithotrophs are important. Lithotrophs are bacteria which use inorganic substrates as an energy source. Lithotrophs consume reduced substances which are electron donors in the process of the generation of energy by the lithotroph. Photolithotrophs alternatively or, usually, additionally consume light to generate energy therefrom. An electron acceptor substance then takes up the electrons. In the case of degradation of chlorinated hydrocarbons, the chlorinated hydrocarbons will generally serve as electron acceptors. In addition to an electron donor substance and an electron acceptor substance, a lithotrophic bacterium needs a carbon source for synthesis of the bacterial cell. Autolithotrophic bacteria use carbon dioxide as a carbon source. Heterolithotrophs need other organic substances for their carbon supply in addition to carbon dioxide.

Complicating factors for the biological degradation are the specific conditions in which the degradation takes place and the fact that currently only one bacterial strain is known which completely degrades chlorinated hydrocarbons to harmless end products. The biological degradation of chlorinated hydrocarbons is particularly carried out by the bacterial group *Dehalococcoides*. Members of the *Dehalococcoides* group are currently the only known bacteria which degrade the soil pollutants tetrachloroethene, trichloroethene, dichloroethenes and vinyl chloride to ethene and ethane. There are other bacteria which can provide a part of the degradation process of tetrachloroethene and trichloroethene, but not the whole degradation process. Therefore, anaerobic bacteria according to the invention comprise *Dehalococcoides* bacteria in a preferred embodiment of the invention. The invention thus provides a method according to the invention in which these anaerobic bacteria comprise *Dehalococcoides* bacteria. The *Dehalococcoides* bacterium is a thin, disc-like organism without a peptidoglycan-like cell wall. The *Dehalococcoides* bacterium is a member of the Green Nonsulfur Bacteria en uses chloroethenes as electron acceptors for its anaerobic respiration. For the degradation of chlorinated hydrocarbons, the *Dehalococcoides* bacteria have various reducing dehalogenases and hydrogenases at their disposal. By means of these enzymes, *Dehalococcoides ethenogenes* is, for instance, capable of converting complex chlorinated hydrocarbons into harmless substances with the aid of hydrogen.

In the field, various techniques have been devised to make the *Dehalococcoides* bacteria grow in order to expedite the sanitation of a soil contaminated with chlorinated hydrocarbons. Firstly, various types of carbons sources are used for this and, secondly, various types of electron donors. However, the carbon sources used in the field are often unsuitable for *Dehalococcoides* bacteria. Use of these carbon sources used in the field usually results in long, non-predictable lag phases, in which no conversion of chlorinated hydrocarbons is measurable. Without wishing to be bound to any theory, it appears likely that the respiration chain of the *Dehalococcoides* group is a precursor of the respiration chains currently present in mitochondria and other bacteria. Due to this limited respiration chain and the absence of essential proteins, enzymes, in the citric acid cycle, the *Dehalococcoides* bacteria have difficulties with glucose, glucose-containing products and the many intermediate substances, which can biologically be derived therefrom, because these bacteria cannot properly convert these substances into energy via their citric acid cycle. Therefore, these substances are not good carbon sources for the *Dehalococcoides* bacteria. Conventional stimulation techniques for the biological degradation of chlorinated hydrocarbons now use carbon sources which often have an inhibitory action on, for instance, *Dehalococcoides* bacteria. The carbon sources provided by the invention can be metabolized by *Dehalococcoides* bacteria; these are acetate and carbon dioxide. In the present sanitation situation, in a method according to the invention, these carbon sources are artificially applied, so that sufficient food is offered to the bacteria. These proteins which the *Dehalococcoides* bacteria lack in the respiration chain and the absent essential proteins of the citric acid cycle, which are normally present in mitochondria and most bacteria, are bypassed in the present invention by artificially adding the nutrients to the anaerobic *Dehalococcoides* bacteria which can be essential to their respiration and growth. En passant, thereby, chlorinated hydrogens are degraded to harmless end products.

As mentioned, most carbon sources currently used are not suitable and the *Dehalococcoides* bacteria react thereto with long lag phases.

Hydrogen is another component which is obligatorily necessary for the *Dehalococcoides* bacteria. In a method according to the invention, hydrogen is also artificially applied to the soils contaminated with chlorinated hydrocarbons, so that, in the conversion of the chlorinated hydrocarbons to harmless products, the pollutants and not the *Dehalococcoides* bacteria are the rate-determining step to begin with. Artificially adding nutrients to soils contaminated with chlorinated hydrocarbons in the form of hydrogen ($H_2$), carbon dioxide ($CO_2$), for instance gaseous hydrogen and gaseous or aqueous carbon dioxide, and acetate, for instance in a solution of water, while the hydrogen is to serve as an electron donor and the other two as carbon sources, is, on the one hand, to ensure that lithotrophic prokaryotes, such as the *Dehalococcoides* group, grow exponentially in anaerobic conditions and, on the other hand, to degrade chlorinated hydrocarbons in an accelerated manner. Here, the chlorinated hydrocarbons serve as electron acceptors.

Bacteria are only capable of showing an optimal activity when the conditions are favorable to these specific bacteria. One of the conditions that are important to bacteria is the pH value of the environment. Therefore, the invention provides a method according to the invention in which a pH value of the soil mentioned is brought within a range which is optimal for the activity of these anaerobic bacteria. The pH value indicates the acidity. With a method according to the invention, the pH can be brought within the range mentioned by actively taking measures for this or, alternatively, the pH in the soil mentioned already is and/or continues to be within this desired range without actively taking further measures for this. An example of a substance which can serve as a buffer component is acetate. Addition of acetate helps to prevent a strong decrease and/or strong increase of the acidity in the soil. In an embodiment of the invention, acetate dissolved in water is thus used to set a pH. So, when the proportions of substances which are added to the soil are determined, the pH, the acidity, of the soil can be taken into account. Here, care should be taken that, for instance, the optimal pH within which the *Dehalococcoides* group operates is preferably not negatively affected by carbon dioxide. Here, it should be noted that, if the carbon dioxide is dissolved in water, bicarbonate is created which can form a buffer with which a pH can be set. In an embodiment of the invention, carbon dioxide dissolved in water is thus used to form a buffer and to set a pH. Further, substances which are, for the rest, not necessary in an embodiment of the invention, can be used to maintain the acidity of the soil within a desired range. A skilled person knows many methods and substances to influence the acidity of a soil.

The pH range that is optimal for the activity of the anaerobic bacteria mentioned will depend on the specific properties of these bacteria, and therefore on the type of anaerobic bacteria. For most bacteria, the pH range for an optimal activity is known and, thus, a skilled person can simply look up the right range for a specific bacterium. Many bacteria show good activity at a more or less neutral pH. In that case, the pH of the soil mentioned is preferably brought within a range of pH 6.5-7.5. An example of anaerobic bacteria which show optimal activity at a more or less neutral pH are *Dehalococcoides* bacteria. Therefore, in a preferred embodiment, the invention provides a method in which the range mentioned of the pH value is preferably 6.0-8.0, more preferably 6.5-7.5, still more preferably 6.7-7.3, and most preferably 6.8-7.2 and in which the anaerobic bacteria mentioned comprise *Dehalococcoides* bacteria.

One of the conditions which is, in addition to the pH value of the environment, important to bacteria for them to be able to carry out an optimal activity is the temperature of the environment. Therefore, in one embodiment, the invention provides a method according to the invention in which the temperature of the soil mentioned is brought within a range which is optimal for the activity of the anaerobic bacteria mentioned. The temperature can be brought within the range mentioned by actively taking measures for this or, alternatively, the temperature in the soil mentioned already is and/or continues to be within the desired range mentioned with a method according to the invention without actively taking further measures for this. A skilled person knows many methods for influencing the temperature of a soil. The temperature of the soil may, for instance, be increased by adding hot gases and/or liquids to the soil and/or using heat mats, a hot addition being an addition which has a temperature which is higher than the temperature of the soil. Conversely, the temperature of the soil may, for instance, be decreased by adding cold gases and/or liquids to the soil, a cold addition being an addition which has a temperature which is lower than the temperature of the soil.

The temperature range which is optimal for the activity of the anaerobic bacteria mentioned will depend on the specific properties of these bacteria, and therefore on the type of anaerobic bacteria. For most bacteria, the temperature range for an optimal activity is known and, thus, a skilled person can simply look up the right range for a specific bacterium. Many bacteria show good activity at a temperature higher than 4° C., often particularly higher than 10° C., and lower than 40° C. In that case, the temperature of the soil mentioned is preferably brought within a temperature range of 4° C.-40° C., more preferably within a temperature range of 10° C.-40° C. An example of anaerobic bacteria which show optimal activity at a temperature range of 4° C.-40° C., particularly within a temperature range of 10° C.-40° C., are *Dehalococcoides* bacteria. Therefore, in a preferred embodiment, the invention provides a method in which the range mentioned is 4° C.-40° C., more preferably 10° C.-40° C., and in which the anaerobic bacteria mentioned comprise *Dehalococcoides* bacteria. In the right conditions, such as pH and temperature, and with the right food, such as the substances which are added according to the invention, the *Dehalococcoides* bacteria degrade the chlorinated hydrocarbons well and fast.

In normal conditions, at room temperature and normal outside temperatures and at normal atmospheric pressure, hydrogen and carbon dioxide are gaseous. So, it is simple and inexpensive to use hydrogen and carbon dioxide in gaseous form. Therefore, in a preferred embodiment of the invention, hydrogen and carbon dioxide are used in gaseous form. For the same reasons of simplicity and price, acetate is preferably used when dissolved in water. In a preferred embodiment, the invention therefore provides a method according to the invention in which the $H_2$ and $CO_2$ mentioned are gaseous and in which the acetate mentioned is dissolved in water. This water comprises any aqueous solution. In a preferred embodiment of the invention, acetate comprises $CH_3COO-$ dissolved in water.

Up to now, in the field, if a substance was added to a soil for in situ acceleration of the biological degradation process, the respective substance was added in a small amount. The single addition was usually at most of the order of a few micromoles. A method according to the invention does not only use multiple necessary substances $H_2$, $CO_2$ and acetate, but also applies each separate substance to the soil in a surprisingly large amount. Although a lower concentration is possible and is within the scope of the invention, a substance according to the invention is preferably applied until groundwater and/or soil are saturated and/or up to a concentration of at least 10 µmol/l of groundwater and/or soil, more preferably up to a concentration of at least 0.1 mmol/l of groundwater and/or soil, more preferably up to a concentration of at least 1 mmol/l of groundwater and/or soil. In a preferred embodiment, the invention therefore provides a method according to the invention in which the $H_2$, $CO_2$ and acetate mentioned are added until the soil mentioned and/or groundwater in the soil mentioned is saturated and/or up to a concentration of at least 10 mmol/l of groundwater and/or soil, more preferably up to a concentration of at least 0.1 mmol/l of groundwater and/or soil, most preferably up to a concentration of at least 1 mmol/l of groundwater and/or soil. The amounts of $H_2$, $CO_2$ and acetate to be added and the concentrations to be reached of course partly depend on the situation. If the substances are, for instance, added to sanitize a pollution source, the amounts to be added which often be larger than if the substances are added to sanitize the associated plume, because the concentrations of chlorinated hydrocarbons in the pollution source will usually be higher than in the plume. In an embodiment of the invention, in a source, preferably concentrations of $H_2$, $CO_2$ and acetate of at least 1 mmol/l of groundwater or soil are reached. In a plume, the concentration of hydrocarbon will usually be lower than in the source and lower concentrations of $H_2$, $CO_2$ and acetate will be sufficient. Since $H_2$, $CO_2$ and acetates are slightly active even with very low concentrations of, for instance, tenths of micromoles per liter, additions which result in low concentrations in the soil are within the scope of the invention.

In a preferred embodiment according to the invention, in addition to $H_2$, $CO_2$ and acetate, still other substances are added to a soil. The other substances which can be added further may be all substances a skilled person would like to add further. The substances according to the invention may be added in any phase conceivable by a skilled person, such as for instance gaseous and/or liquid. In an embodiment according to the invention, the other substances are preferably nutrients for anaerobic bacteria. These nutrients for anaerobic bacteria are all substances which play a role in the life of these anaerobic bacteria. Examples of substances which form important nutrients for many anaerobic bacteria are nitrogen, phosphate and magnesium. In one embodiment, the invention therefore provides a method according to the invention in which, to the soil mentioned, further, the substances phosphate and/or nitrogen and/or magnesium are added. Phosphate and/or nitrogen and/or magnesium and/or other substances which can be added to a soil according to the invention may be added in any form, for instance pure substances and/or simple compounds and/or complex compounds and/or mixtures, as long as the respective form is a source of the respective substance for anaerobic bacteria.

Addition of substances to a soil according to a method of the invention can take place in all possible manners. A skilled person knows many methods for adding substances to a soil. A soil is, for instance, added to a soil contaminated with chlorinated hydrocarbon with the aid of injections or other aids. Any manner of addition is suitable as long as the added substance reaches the area contaminated with chlorinated hydrocarbon and preferably reaches a concentration of at least 10 µmol/l, more preferably of at least 0.1 mmol/l, most preferably of at least 1 mmol/l. An example of a suitable manner of adding substances according to a method of the invention is injecting substances. Substances which are added in gaseous form are, in such a method, preferably injected below an area comprising chlorinated hydrocarbon and/or into an area comprising chlorinated hydrocarbon. Substances which are added in liquid and/or dissolved form are, in such a method, preferably injected into an area comprising this chlorinated hydrocarbon and/or above an area comprising this chlorinated hydrocarbon. In one embodiment, the invention therefore provides a method according to the invention in which, in the soil mentioned, above-mentioned gaseous $H_2$ and/or $CO_2$ and any other gaseous substances to be added are at least injected below an area comprising this chlorinated hydrocarbon and in which above-mentioned acetate and any other liquid and/or dissolved substances to be added are at least injected into an area comprising this chlorinated hydrocarbon. In methods as used in the field, what it usually comes down to is that the gaseous nutrients are injected far below the pollution source and plume and that the gases then automatically diffuse upwards. On their way up, these gases encounter those bacteria that need these gases for the respiration and growth. En passant, thereby, chlorinated hydrocarbons are converted into harmless substances. The necessary aqueous substances are usually injected into the source and plume.

The gaseous substances added in a method according to the invention are preferably added at a pressure which does not differ too much from a pressure in the soil to prevent the gases from escaping at the surface without first saturating the soil.

The biostimulation, gaseous in a preferred embodiment of the invention, which is carried out artificially in combination with application of some other bacterial nutrients to the soil, serves the purpose of sanitizing soils contaminated with chlorinated hydrocarbons in an accelerated manner at strongly reduced costs compared to conventional sanitation methodologies. The carbon dioxide supplemented by acetate, for instance dissolved in water, and further, for instance, a phosphate and a nitrogen source, are responsible for the growth of the anaerobic bacteria. Both gases, $H_2$ and $CO_2$, in any possible proportion to each other, optionally diluted with gaseous nitrogen, another gas and other nutrients in combination with acetate dissolved in water, phosphate and a nitrogen source, are simultaneously or each separately added to the contaminated soils with the aid of injections or other aids, while they are offered there to anaerobic bacteria, such as the *Dehalococcoides* bacteria, in overmeasure. Accordingly, after a short incubation, stimulation and a growth period of the anaerobic bacteria, not the number of bacteria per volume unit, but particularly the amount of electron acceptors in the form of chlorinated hydrocarbons is the rate-determining step in the further growth of the bacteria.

Because of the lithotrophic properties of many anaerobic bacteria, including the *Dehalococcoides* bacteria, reduction of the costs, simplicity and convenience of the present method, in an embodiment of the invention, a deliberate choice was made for acetate dissolved in water as a primary carbon source in combination with gaseous carbon dioxide ($CO_2$) as a secondary carbon source. With acetate as a primary carbon source in addition to sufficient anaerobic bacteria, preferably *Dehalococcoides* bacteria, per volume unit, and hydrogen as an electron donor, half-lives for chlorinated hydrocarbons in polluted soils of a few hours can be achieved. Here, *Dehalococcoides* bacteria show the best activity in strictly anaerobic conditions, where hydrogen acts as an electron carrier, carbon dioxide and acetate as carbon sources and chlorinated hydrocarbons as electron acceptors. Since a method according to the invention is very suitable for accelerating biological degradation of chlorinated hydrocarbons in a soil by means of *Dehalococcoides bacteria* and *Dehalococcoides* bacteria are capable of degrading tetrachloroethene (also called perchloroethene) and trichloroethene to ethene and ethane, in an embodiment of the invention, chlorinated hydrocarbon comprises inter alia tetrachloroethene and trichloroethene. *Dehalococcoides* bacteria can also degrade, for instance, dichloroethene, vinyl chloride and a polychlorinated biphenyl compound to ethene and ethane. In one embodiment, the invention therefore provides a method according to the invention for in situ acceleration of biological degradation of chlorinated hydrocarbons in a soil, in which this chlorinated hydrocarbon is tetrachloroethene and/or thrichloroethene and/or a dichloroethene and/or vinyl chloride and/or a polychlorinated biphenyl compound.

In a further aspect, the invention provides use of $H_2$, $CO_2$ and acetate for in situ biological degradation or in situ acceleration of biological degradation of chlorinated hydrocarbons in a soil. These substances may be used in any concentration and in any phase. Preferably, $H_2$ is used as pure $H_2$ under pressure, $CO_2$ is used as pure $CO_2$ under pressure and/or in a liquid form and acetate is used as acetate in an aqueous solution. In addition to $H_2$, $CO_2$ and acetate, according to the invention, any other substance may be used, such as for instance one or more auxiliary substances. Preferably, according to the invention, nutrients for anaerobic bacteria, such as phosphate and/or nitrogen and/or magnesium are used.

Artificially adding nutrients to soils contaminated with chlorinated hydrocarbons in the form of gaseous hydrogen ($H_2$) and gaseous carbon dioxide ($CO_2$), as an electron donor and a carbon source, respectively, is, on the one hand, to ensure that lithotrophic prokaryotes, such as the *Dehalococcoides* group, exponentially grow in anaerobic conditions and, on the other hand, to degrade chlorinated hydrocarbons in an accelerated manner. Here, these chlorinated hydrocarbons serve as electron acceptors. The carbon dioxide supplemented by acetate dissolved in water, phosphate and a nitrogen source is responsible for the growth of the anaerobic bacteria.

This gaseous biostimulation, which is artificially applied to the soils in combination with some other bacterial nutrients, serves the purpose of sanitizing soils contaminated with chlorinated hydrocarbons in an accelerated manner at strongly reduced costs compared to conventional sanitation methodologies.

Both gases, in any possible proportion to each other, optionally diluted with gaseous nitrogen, another gas and other nutrients in combination with acetate dissolved in water, phosphate and a nitrogen source, are simultaneously or each separately added to the contaminated soils with the aid of injections or other aids, where they are offered to anaerobic bacteria, such as the *Dehalococcoides* bacteria, in overmeasure. Accordingly, after a short incubation, stimulation and a growth period of the anaerobic bacteria, not the number of bacteria per volume unit, but particularly the amount of electron acceptors in the form of chlorinated hydrocarbons is the rate-determining step in the further growth of the bacteria.

With acetate as a primary carbon source in addition to sufficient anaerobic bacteria, preferably *Dehalococcoides* bacteria, per volume unit, and hydrogen as an electron donor, half-lives for chlorinated hydrocarbons in polluted soils of a few hours can be achieved.

Because of the lithotrophic properties of many anaerobic bacteria, including the *Dehalococcoides* bacteria, reduction of the costs, simplicity and convenience of the present method, in an embodiment of the invention, a deliberate choice was made for acetate dissolved in water as a primary carbon source in combination with gaseous carbon dioxide ($CO_2$) as a secondary carbon source.

Members of the *Dehalococcoides* group are currently the only known bacteria which degrade the soil pollutants tetrachloroethene and trichloroethene to ethene and ethane. For this, the *Dehalococcoides* bacteria have various reducing dehalogenases and hydrogenases at their disposal. By means of these enzymes, *Dehalococcoides ethenogenes* is, for instance, capable of converting complex chlorinated hydrocarbons into harmless substances with the aid of hydrogen.

The *Dehalococcoides* bacterium is a thin, disc-like organism without a peptidoglycan-like cell wall. The *Dehalococcoides* bacterium is a member of the Green Nonsulfur Bacteria en uses chloroethenes as electron acceptors for its anaerobic respiration.

It is likely that the respiration chain of the *Dehalococcoides* group is a precursor of the respiration chains currently present in mitochondria and other bacteria. Due to this limited respiration chain and the absence of essential enzymes in the citric acid cycle, the *Dehalococcoides* bacteria have difficulties with glucose, glucose-containing products and the many intermediate substances, which can biologically be derived therefrom. Therefore, these substances are not good carbon sources for the *Dehalococcoides* bacteria.

Use of these carbon sources usually results in long, non-predictable lag phases, in which no conversion of chlorinated hydrocarbons is measurable.

The carbon sources which can be metabolized by *Dehalococcoides* bacteria are acetate and carbon dioxide.

Chlorinated hydrocarbons are good fat solvents. Therefore these substances are frequently used in the metal industry and in dry cleaning. Thereby, up to the 1980s, large amounts of chlorinated hydrocarbons have ended up in the ground to severely pollute the soils there. Removing these pollutants is difficult and complex.

This is because chlorinated hydrocarbons are heavier than water, so that they may be present in the soil to a great depth in high concentrations. In addition, they only slowly pass into dissolution and they thus form secondary pollution sources for long periods, which are to be sanitized to prevent further pollution.

Currently, biological degradation of these chlorinated hydrocarbons is the most effective manner of sanitation. This biological degradation is mainly carried out by the bacterial group *Dehalococcoides*. As stated, this is done in strictly anaerobic conditions with hydrogen as an electron carrier, carbon dioxide and acetate as carbon sources and chlorinated hydrocarbons as electron acceptors.

In the right conditions, such as pH and temperature, and with the right food, the *Dehalococcoides* bacteria degrade the chlorinated hydrocarbons well and fast.

Complicating factors for this biological degradation are the specific conditions in which the degradation takes place and the fact that currently only one bacterial strain is known which completely degrades chlorinated hydrocarbons to harmless end products.

In order to expedite the sanitation of chlorinated hydrocarbons, various techniques have been devised to make this bacterial strain grow. Firstly, various types of carbons sources are used for this and, secondly, various types of electron donors.

As previously mentioned, most carbon sources currently used are unsuitable and *Dehalococcoides* bacteria react thereto with long lag phases.

*Dehalococcoides* bacteria are lithotrophic, that is to say that carbon dioxide is one of their carbon sources. The other carbon source is acetate. In the present sanitation situation, these carbon sources are artificially applied, so that sufficient food is offered to the bacteria. Here, care should be taken that the optimal pH within which the *Dehalococcoides* group operates is not negatively affected by the carbon dioxide.

Hydrogen is another component which is obligatorily necessary for the *Dehalococcoides* bacteria. This gas is also artificially applied to the soils contaminated with chlorinated hydrocarbons, so that, in the conversion of the chlorinated hydrocarbons to harmless products, the pollutants and not the *Dehalococcoides* bacteria are the rate-determining step to begin with.

In the biostimulations currently used, carbon dioxide, acetate and/or hydrogen are the limiting factors. This results in long, no n-predictable lag phases. With the present approach of the invention, a solution is found for this by artificially offering both gases and dissolved acetate in overmeasure. What it usually comes down to is that the gaseous nutrients are injected far below the pollution source and plume and that the gases then automatically diffuse upwards. On their way up, these gases encounter bacteria which need these gases for the respiration and growth. En passant, thereby, chlorinated hydrocarbons are converted into harmless substances. The necessary aqueous substances are usually injected into the source and plume.

All techniques which serve to contact the gaseous nutrients hydrogen and carbon dioxide and the aqueous acetate solution with *Dehalococcoides* bacteria in a safe and responsible manner, so that they can use the chlorinated hydrocarbons for their respiration, are covered by this patent.

In one embodiment, the invention provides an in situ soil decontamination method for the biological degradation of chlorinated hydrocarbons in soils, characterized in that, for this biological decontamination, gas mixtures consisting of hydrogen and carbon dioxide and acetate dissolved in water are applied to the soils from external sources for stimulation and support of the respiration chain and growth of anaerobic bacteria, including the *Dehalococcoides* bacterial group, so that they biologically degrade the chlorinated hydrocarbons in an accelerated manner. In a further embodiment, the invention provides that above-mentioned external application used of gas mixtures consisting of hydrogen and carbon dioxide and acetate dissolved in water also holds for all soils contaminated with chlorinated hydrocarbons, where the respective bacteria have been added to these soils from another location. Above-mentioned gas mixtures used of hydrogen and carbon dioxide can be added to the soil each separately or simultaneously in any conceivable proportion, optionally diluted with other gases and auxiliary substances, but in any case simultaneously or separately with acetate dissolved in water in a safe, efficient and adequate manner with the aid of any aid suitable for this. Further, above-mentioned gas mixtures and liquids used may be applied to the soils contaminated with chlorinated hydrocarbons in one go or gradually at any conceivable rate, amount and frequency, while the location and depth of the gas mixtures to be used depends on the location of the pollution, so that an optimal biostimulation for the degradation of the chlorinated hydrocarbons is created. Further, any aid and form of application for applying the above-mentioned nutrients to the contaminated soils falls within the scope of this invention.

The invention relates to the in situ biostimulation of anaerobic bacteria, including the *Dehalococcoides* bacteria, with the aid of gaseous nutrients, such as hydrogen and carbon dioxide in combination with acetate dissolved in water in soils contaminated with chlorinated hydrocarbons. These nutrients are applied to these soils, for the purpose of biologically sanitizing these soils in an accelerated and cost-effective manner.

Currently, *Dehalococcoides* bacteria are the only prokaryotes which degrade tetrachloroethene and trichloroethene to ethene. For this, these bacteria have various dehalogenases and hydrogenases at their disposal. Here, hydrogen serves as an electron donor. The carbon sources for these *Dehalococcoides* bacteria are carbon dioxide and acetate. For their anaerobic respiration, they exclusively use chlorinated hydrocarbons.

The gaseous nutrients and nutrients dissolved in water which are artificially used for biostimulation of anaerobic bacteria, including the *Dehalococcoides* group, can safely and adequately be applied to the soils contaminated with chlorinated hydrocarbons in any possible proportion, rate and amount, in such a manner that an optimal biostimulation is created. These forms of application are claimed as well.

Conventional stimulation techniques for the biological degradation of chlorinated hydrocarbons now use carbon sources which often have an inhibitory action on, for instance, *Dehalococcoides* bacteria, because these bacteria cannot convert these substances into energy via their citric acid cycle. They lack essential proteins for this, which are normally present in mitochondria and most bacteria, in the respiration chain and the citric acid cycle.

In the present invention, these proteins are bypassed by artificially adding nutrients to the anaerobic *Dehalococcoides* bacteria, which are essential to their respiration and growth. En passant, here, chlorinated hydrogens are degraded to harmless end products.

A hyphen between numbers as used in the claims and specification of the invention, is to be understood to mean: up to and including. So, for instance: claims 1-12 is to be read as: claims 1 up to and including 12. The invention is further explained by the following examples. The examples are not to be taken as limiting the protective scope of the invention in any way.

The invention claimed is:

1. A method for in situ acceleration of biological degradation of chlorinated hydrocarbons in a soil, the method comprising:
    adding to said soil essentially simultaneously at least the following essential substances: $H_2$, $CO_2$ and acetate, wherein said soil comprises *Dehalococcoides* bacteria.

2. The method according to claim 1, wherein part of said *Dehalococcoides* bacteria have been added to said soil.

3. The method according to claim 1, wherein a pH value of said soil is brought within a range which is optimal for activity of said *Dehalococcoides* bacteria.

4. The method according to claim 3, wherein said range is pH value 6.5-7.5.

5. The method according to claim 1, wherein the temperature of said soil is brought within a range which is optimal for activity of said *Dehalococcoides* bacteria.

6. The method according to claim 5, wherein said range is 4° C-40° C.

7. The method according to claim 1, wherein said $H_2$ is gaseous and wherein said acetate is dissolved in water and wherein the $CO_2$ is gaseous or dissolved in water.

8. The method according to claim 1, wherein said $H_2$, $CO_2$ and acetate are added up to a concentration of at least 10 μmol/l of soil.

9. The method according to claim 1, wherein, to said soil, further, a substance selected from the group consisting of phosphate, nitrogen, and magnesium is added.

10. The method according to claim 7, wherein, in said soil, said gaseous $H_2$ and/or $CO_2$ are at least injected below an area comprising said chlorinated hydrocarbon and wherein said acetate is at least injected into an area comprising said chlorinated hydrocarbon.

11. The method according to claim 1, wherein said chlorinated hydrocarbons comprise chlorinated hydrocarbons selected from the group consisting of tetrachloroethene, trichloroethene, a dichloroethene, vinyl chloride, a polychlorinated biphenyl compound, and mixtures thereof.

12. A method of in situ biological degradation of chlorinated hydrocarbons in a soil, the method comprising:
    adding hydrogen ($H_2$), carbon dioxide ($CO_2$), and acetate essentially simultaneously to accelerate in situ biological degradation of the chlorinated hydrocarbons in the soil; and
    wherein the soil comprises *Dehalococcoides* bacteria.

13. A method for degrading chlorinated hydrocarbons present in soil, the method comprising:
    adding anaerobic bacteria to the soil, wherein said anaerobic bacteria comprise *Dehalococcoides* bacteria;
    adding at least hydrogen ($H_2$), carbon dioxide ($CO_2$), and acetate to the soil essentially simultaneously;
    bringing the soil's pH to a value of from about 6.5 to about 7.5;

bringing the soil's temperature to between about 4° C. and about 40° C.; and thus degrading chlorinated hydrocarbons in the soil.

14. The method according to claim 13, wherein the $H_2$ and $CO_2$ are gaseous and wherein the acetate is dissolved in water.

15. The method according to claim 13, further comprising adding phosphate, nitrogen, and/or magnesium.

16. The method according to claim 14, wherein, in the soil, the gaseous $H_2$ and/or $CO_2$ are at least injected below an area comprising the chlorinated hydrocarbon and wherein the acetate is at least injected into an area comprising the chlorinated hydrocarbon.

17. The method according to claim 13, wherein said chlorinated hydrocarbons comprise chlorinated hydrocarbon selected from the group consisting of tetrachloroethene, trichloroethene, dichloroethene, vinyl chloride, polychlorinated biphenyl compound, and mixtures of any thereof.

18. A anaerobic method for in situ acceleration of biological degradation of chlorinated hydrocarbons in a soil, the method comprising:

adding to said soil essentially simultaneously at least the following essential substances: $H_2$, $CO_2$ and acetate, wherein said soil comprises *Dehalococcoides* bacteria.

* * * * *

UNITED STATES PATENT AND TRADEMARK OFFICE
CERTIFICATE OF CORRECTION

PATENT NO.       : 8,372,627 B2
APPLICATION NO.  : 11/908490
DATED            : February 12, 2013
INVENTOR(S)      : Gerhardus Johannes Jozef Beukeveld It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1379 days.

Signed and Sealed this
First Day of September, 2015

Michelle K. Lee
*Director of the United States Patent and Trademark Office*